(12) United States Patent
Bui et al.

(10) Patent No.: US 10,448,643 B2
(45) Date of Patent: Oct. 22, 2019

(54) LOW PH DISINFECTANT COMPOSITION

(71) Applicant: Medivators Inc., Minneapolis, MN (US)

(72) Inventors: Huyen Phuong Bui, Brooklyn Park, MN (US); Adam W. Hauser, Minneapolis, MN (US); Thomas M. Gentle, St. Michael, MN (US); Jonathan K. Olson, Delano, MN (US); John J. Matta, Shoreview, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 15/876,523

(22) Filed: Jan. 22, 2018

(65) Prior Publication Data

US 2018/0139965 A1    May 24, 2018

Related U.S. Application Data

(62) Division of application No. 15/592,771, filed on May 11, 2017, now Pat. No. 9,901,100, which is a division of application No. 15/261,009, filed on Sep. 9, 2016, now Pat. No. 9,655,368, which is a division of application No. 14/366,287, filed as application No. PCT/US2012/071977 on Dec. 28, 2012, now Pat. No. 9,445,600.

(60) Provisional application No. 61/581,519, filed on Dec. 29, 2011, provisional application No. 61/608,324, filed on Mar. 8, 2012.

(51) Int. Cl.

| | |
|---|---|
| *A01N 59/00* | (2006.01) |
| *A01N 31/02* | (2006.01) |
| *A01N 31/08* | (2006.01) |
| *A01N 55/00* | (2006.01) |
| *A01N 25/08* | (2006.01) |
| *D06M 11/50* | (2006.01) |
| *D06M 13/144* | (2006.01) |
| *D06M 13/463* | (2006.01) |
| *A01N 25/22* | (2006.01) |
| *A01N 25/30* | (2006.01) |
| *D06M 11/70* | (2006.01) |
| *D06M 13/165* | (2006.01) |
| *D06M 13/352* | (2006.01) |
| *D06M 13/513* | (2006.01) |

(52) U.S. Cl.
CPC ............ *A01N 59/00* (2013.01); *A01N 25/08* (2013.01); *A01N 25/22* (2013.01); *A01N 25/30* (2013.01); *A01N 31/02* (2013.01); *A01N 31/08* (2013.01); *A01N 55/00* (2013.01); *D06M 11/50* (2013.01); *D06M 11/70* (2013.01); *D06M 13/144* (2013.01); *D06M 13/165* (2013.01); *D06M 13/352* (2013.01); *D06M 13/463* (2013.01); *D06M 13/513* (2013.01)

(58) Field of Classification Search
CPC ............................... A01N 59/00; A01N 55/00
See application file for complete search history.

(56) References Cited

U.S. PATENT DOCUMENTS

| | | | |
|---|---|---|---|
| 4,900,721 | A | 2/1990 | Bansemir et al. |
| 5,891,392 | A | 4/1999 | Monticello et al. |
| 6,106,774 | A | 8/2000 | Monticello et al. |
| 6,821,943 | B2 | 11/2004 | Avery et al. |
| 8,999,399 | B2 | 4/2015 | Lisowsky et al. |
| 9,265,248 | B2 | 2/2016 | Gentle et al. |
| 9,445,600 | B2 | 9/2016 | Bui et al. |
| 9,655,368 | B2 | 5/2017 | Bui et al. |
| 9,901,100 | B2 | 2/2018 | Bui et al. |
| 2003/0073600 | A1 | 4/2003 | Avery et al. |
| 2007/0258915 | A1 | 11/2007 | Kielbania |
| 2011/0262557 | A1 | 10/2011 | Omidbakhsh |
| 2014/0322285 | A1 | 10/2014 | Bui et al. |
| 2016/0374347 | A1 | 12/2016 | Bui et al. |
| 2017/0245502 | A1 | 8/2017 | Bui et al. |

FOREIGN PATENT DOCUMENTS

| | | |
|---|---|---|
| AU | 2012362306 B2 | 6/2016 |
| CN | 1237203 A | 12/1999 |
| CN | 104023532 A | 9/2014 |
| CN | 104023532 B | 11/2017 |
| EP | 2797415 B1 | 12/2017 |
| WO | WO-0035289 A1 | 6/2000 |
| WO | WO-2000035289 A1 | 6/2000 |
| WO | WO-2010037219 A1 | 4/2010 |

(Continued)

OTHER PUBLICATIONS

"U.S. Appl. No. 14/366,287, Applicant's Summary filed Sep. 15, 2016 to Examiner Interview Summary dated Aug. 12, 2016", 1 pg.

(Continued)

*Primary Examiner* — Gina C Justice

(74) *Attorney, Agent, or Firm* — Schwegman Lundberg & Woessner, P.A.

(57) ABSTRACT

The invention provides for a low pH disinfectant composition that includes a relatively low amount of alcohol. Also provided is an article of manufacture that includes a textile and the composition, as well as methods of using the composition and article of manufacture (e.g., for reducing the number of microbes located upon a substrate, for killing or inhibiting a broad spectrum of microorganisms, for killing or inhibiting spore forming bacteria, and/or for disinfecting a substrate). The composition can optionally include a stable residual antimicrobial compound, thereby providing a combination of high-level disinfection and long-lasting residual effect.

14 Claims, No Drawings

(56) References Cited

FOREIGN PATENT DOCUMENTS

WO    WO-2013102021 A2    7/2013
WO    WO-2013102021 A3    7/2013

OTHER PUBLICATIONS

"U.S. Appl. No. 14/366,287, Examiner Interview Summary dasted Aug. 17, 2016", 2 pgs.
"U.S. Appl. No. 14/366,287, Non Final Office Action dated Oct. 2, 2015", 14 pgs.
"U.S. Appl. No. 14/366,287, Notice of Allowability dated Aug. 17, 2016", 6 pgs.
"U.S. Appl. No. 14/366,287, Notice of Allowance dated May 16, 2016", 10 pgs.
"U.S. Appl. No. 14/366,287, Response filed Sep. 11, 2015 to Restriction Requirement dated May 12, 2015", 10 pgs.
"U.S. Appl. No. 14/366,287, Restriction Requirement dated May 12, 2015", 10 pgs.
"U.S. Appl. No. 15/261,009, Notice of Allowance dated Jan. 20, 2017", 9 pgs.
"U.S. Appl. No. 15/261,009, PTO Response to Rule 312 Communication dated Apr. 4, 17", 2 pgs.
"U.S. Appl. No. 15/592,771, Notice of Allowance dated Oct. 25, 2017", 5 pgs.
"U.S. Appl. No. 15/592,771, Preliminary Amendment filed May 12, 17", 80 pgs.
"U.S. Appl. No. 14/366,287, Preliminary Amendment filed Jun. 18, 2014", 12 pgs.
"U.S. Appl. No. 14/366,287, Response filed Feb. 2, 2016 to Non-Final Office Action dated Oct. 2, 2015", 11 pgs.
"Australian Application Serial No. 202362306, First Examiner Report dated Sep. 11, 2015", 4 pgs.
"Australian Application Serial No. 2012362306, Response filed Feb. 10, 2016 to First Examiner Report dated Sep. 11, 2015", 21 pgs.
"Australian Application Serial No. 2012362306, Response filed May 25, 2016 to Subsequent Examiners Report dated Mar. 10, 2016", 9 pgs.
"Australian Application Serial No. 2012362306, Subsequent Examiners Report dated Mar. 10, 2016", 3 pgs.
"Chinese Application Serial No. 201280064610.7, Office Action dated Feb. 16, 2016", with English translation, 12 pgs.
"Chinese Application Serial No. 201280064610.7, Office Action dated Feb. 28, 2017", With English Translation, 8 pgs.
"Chinese Application Serial No. 201280064610.7, Office Action dated Jun. 17, 15", (w/ English Translation), 13 pgs.
"Chinese Application Serial No. 201280064610.7, Office Action dated Aug. 16, 2016", (English Translation), 12 pgs.
"Chinese Application Serial No. 201280064610.7, Response filed Apr. 11, 2016 to Office Action dated Feb. 16, 2016", (English Translation of Claims), 20 pgs.
"Chinese Application Serial No. 201280064610.7, Response Filed May 11, 2017 to Office Action dated Feb. 28, 2017", (W/ English Claims), 18 pgs.
"Chinese Application Serial No. 201280064610.7, Response filed Oct. 17, 2016 to Office Action dated Aug. 16, 2016", with English Claims, 18 pgs.
"Chinese Application Serial No. 201280064610.7, Response filed Oct. 19, 2015 to Office Action dated Jun. 17, 2015", (w/ English Translation of Claims), 19 pgs.
"European Application Serial No. 12815972.0, Communication Pursuant to Article 94(3) EPC dated Jan. 18, 2017", 3 pgs.
"European Application Serial No. 12815972.0, Communication Pursuant to Article 94(3) EPC dated Jul. 6, 2016", 3 pgs.
"European Application Serial No. 12815972.0, Office Action dated Oct. 22, 2015", 4 pgs.
"European Application Serial No. 12815972.0, Response filed Jan. 14, 2016 to Office Action dated Oct. 22, 2015", 11 pgs.
"European Application Serial No. 12815972.0, Response Filed Feb. 28, 2017 to Communication Pursuant to Article 94(3) EPC dated Jan. 18, 2017", 60 pgs.
"European Application Serial No. 12815972.0, Response filed Oct. 11, 2016 to Communication Pursuant to Article 94(3) EPC dated Jul. 6, 2016", 4 pgs.
"International Application Serial No. PCT/US2012/071977, International Preliminary Report on Patentability dated Jul. 10, 2014", 7 pgs.
"International Application Serial No. PCT/US2012/071977, International Search Report dated Jan. 17, 2014", 4 pgs.
"International Application Serial No. PCT/US2012/071977, Written Opinion dated Jan. 17, 2014" 5 pgs.

LOW PH DISINFECTANT COMPOSITION

CLAIM OF PRIORITY

This application is a divisional application of U.S. patent application Ser. No. 15/592,771, filed May 11, 2017, entitled "LOW pH DISINFECTANT COMPOSITION", which is a divisional application of U.S. patent application Ser. No. 15/261,009, filed Sep. 9, 2016, entitled "LOW pH DISINFECTANT COMPOSITION," which is a divisional application of U.S. patent application Ser. No. 14/366,287, filed on Jun. 18, 2014, entitled "LOW pH DISINFECTANT COMPOSITION," which is a U.S. National Stage application filed under 35 U.S.C. § 371 from International Application Serial No. PCT/US2012/071977, filed on Dec. 28, 2012, entitled "LOW DISINFECTANT COMPOSITION," which claims the benefit of priority of U.S. Provisional Patent Application Ser. No. 61/581,519, entitled "LOW pH DISINFECTANT COMPOSITION," filed on Dec. 29, 2011, and claims the benefit of priority of U.S. Provisional Patent Application Ser. No. 61/608,324, entitled "LOW pH DISINFECTANT COMPOSITION," filed on Mar. 8, 2012, which applications and publication are incorporated by reference as if reproduced herein and made a part hereof in their entirety, and the benefit of priority of each of which is claimed herein.

SUMMARY OF THE INVENTION

The invention provides for a composition that can achieve a high-level of disinfection. The composition has a relatively high level of material compatibility, and is relatively safe for use in disinfecting a wide-spectrum of substrates. The composition includes a relatively low amount (e.g., less than about 50 wt. %) of alcohol, and a relatively low (e.g., less than about 4.5) PH. At a pH of about 3, the combination of alcohol (e.g., isopropyl alcohol), hydrogen peroxide, thymol, surfactant, stabilizer, and corrosion inhibitor can inactivate up to about 6 logs of microorganisms such as, e.g., *Mycobacterium terrae* in about 2 minutes or less. This composition, without inhibiting its quick kill times, can also include a stable residual antimicrobial compound (e.g., a quaternary ammonium silane compound, such as 3-(trimethoxysilyl)propyl dimethyl octadecyl ammonium chloride), thereby providing a combination of high-level disinfection and long-lasting residual effect. In achieving a high-level of disinfection, in specific embodiments, the composition can kill and/or inactivate spores. In additional specific embodiments, the composition can kill and/or inactivate a broad spectrum of microorganisms. Additionally, the high-level disinfection and long-lasting residual effect can be accomplished with the use of a composition that employs a relatively low amount (e.g., less than about 50 wt. %) of alcohol, and a relatively low (e.g., less than about 4.5) pH. Additionally, in specific embodiments, the composition is formulated such that the growth of spore forming bacteria is prevented, or diminished. This will minimize the likelihood that cross-contamination will occur during the manufacturing process, which can occur more readily with higher alcohol-based products.

The invention provides for a composition that includes: $(C_1-C_8)$alkyl substituted with one or more hydroxyl, hydrogen peroxide ($H_2O_2$), thymol isopropyl-5-methylphenol), optionally an antimicrobial agent, surfactant, corrosion inhibitor, acid sufficient to maintain the pH below about 4.5, and water.

In specific embodiments, the invention provides for a composition that includes: isopropyl alcohol (2-propanol), optionally ([(3-trimethoxysilyl)propyl] octadecyldimethylammonium chloride) (TPAC), hydrogen peroxide ($H_2O_2$), thymol (2-isopropyl-5-methylphenol), Plutonic® L44 polaxamer 124, 2-butoxyethanol, Tergitol® 15-S-12 surfactant, benzotriazole, phosphoric acid, and de-ionized water.

In more specific embodiments, the invention provides for a composition that includes: about 21 wt. % isopropyl alcohol (2-propanol), about 0.5 wt. % ([(3-trimethoxysilyl)propyl]octadecyldimethylammonium chloride) (TPAC), about 4.0 wt. % hydrogen peroxide ($H_2O_2$), about 0.2 wt. % thymol (2-isopropyl-5-methylphenol), about 0.2 wt. % Pluronic® L44 polaxamer 124, about 5.0 wt. % 2-butoxyethanol, about 0.5 wt. % Tergitol® 15-S-12 surfactant, about 0.1 wt. % benzotriazole, phosphoric acid, sufficient to bring the pH to less than about 3.5, and de-ionized water (q.s.).

In specific embodiments, the invention provides for an article of manufacture that includes a textile and a composition. The composition is located on the surface of the textile, the composition is at least partially embedded within the textile, or a combination thereof. The composition is described herein.

In specific embodiments, the invention provides for a method of reducing the number of microbes located upon a substrate. The method includes contacting the substrate with an effective amount of a composition described herein, for a sufficient period of time, effective to reduce the number of microbes located upon the substrate.

In specific embodiments, the invention provides for a method of killing or inhibiting a microorganism. The method includes contacting the microorganism with an antimicrobially effective amount of a composition described herein, for a sufficient period of time, effective to kill or inhibit the microorganism.

In specific embodiments, the invention provides for a method of disinfecting a substrate. The method includes contacting the substrate with an effective amount of a composition described herein, for a sufficient period of time, effective to disinfect the substrate.

DETAILED DESCRIPTION OF THE INVENTION

Reference will now be made in detail to certain claims of the present invention, examples of which are illustrated in the accompanying structures and formulas. While the disclosed invention will be described in conjunction with the enumerated claims, it will be understood that the disclosed invention is not intended to limit those claims. On the contrary, the disclosed invention is intended to cover all alternatives, modifications, and equivalents, which can be included within the scope of the present invention, as defined by the claims.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not only the explicitly recited amount of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range.

The present invention relates to compositions that can achieve a high-level of disinfection, methods of using the compositions, and/or kits that include the compositions. In specific embodiments, the composition includes: $(C_1$-$C_8)$ alkyl substituted with one or more hydroxyl, hydrogen peroxide $(H_2O_2)$, thymol (2-isopropyl-5-methylphenol), optionally an antimicrobial agent, surfactant, corrosion inhibitor, acid sufficient to maintain the pH below about 4.5, and water. When describing the present invention, the following terms have the following meanings, unless otherwise indicated.

The term "about" can allow for a degree of variability in a value or range, for example, within 10%, within 5%, or within 1% of a stated value or of a stated limit of a range.

Alcohol

The term "hydroxyl" or "hydroxy" refers to the group —OH.

The term "alcohol" refers to a compound that includes one or more hydroxyl groups. The term "polyol" refers to a compound that includes two or more hydroxyl groups. As such, polyols are a sub-group of alcohols.

The term "$(C_1$-$C_8)$alkyl substituted with one or more hydroxyl" refers to a fully saturated hydrocarbon (branched or straight-chained, linear molecule composed of hydrogen and carbon atoms) that includes one or more hydroxyl groups, each substituted on a carbon atom of the hydrocarbon. In specific embodiments, the $(C_1$-$C_8)$alkyl substituted with one or more hydroxyl can include an alcohol, present in any suitable and affective amount. In more specific embodiments, the $(C_1$-$C_8)$alkyl substituted with one or more hydroxyl can include an alcohol, present in less than about 50 wt. % of the composition. In more specific embodiments, the $(C_1$-$C_8)$alkyl substituted with one or more hydroxyl can include an alcohol, present in less than about 35 wt. % of the composition. In more specific embodiments, the $(C_1$-$C_8)$ alkyl substituted with one or more hydroxyl can include an alcohol, present in less than about 25 wt. % of the composition. In additional specific embodiments, the $(C_1$-$C_8)$alkyl substituted with one or more hydroxyl can include isopropyl alcohol (2-propanol). In more specific embodiments, the $(C_1$-$C_8)$alkyl substituted with one or more hydroxyl can include isopropyl alcohol (2-propanol), present in about 10 wt. % to about 30 wt. % of the composition.

An additional suitable alcohols includes, ethanol and glycerol.

Thymol

The term "thymol" or "2-isopropyl-5-methylphenol" refers to a monoterpene phenol derivative of cymene, $C_{10}H_{14}O$, isomeric with carvacrol, found in oil of thyme, and extracted from *Thymus vulgaris* (common thyme) and various other kinds of plants as a white crystalline substance of a pleasant aromatic odor and strong antiseptic properties. Thymol also provides the distinctive, strong flavor of the culinary herb thyme, also produced from *T. vulgaris*. Thymol has the CAS Reg. No. 89-83-9, and the chemical structure shown below:

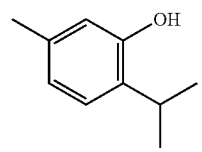

thymol

The thymol can be present in any suitable and effective amount. In specific embodiments, the thymol can be present in about 0.01 wt. % to about 2.0 wt. % of the composition. In more specific embodiments, the thymol can be present in about 0.05 wt. % to about 1.0 wt. % of the composition. In more specific embodiments, the thymol can be present in about 0.2 wt. % of the composition.

Hydrogen Peroxide

The term "hydrogen peroxide" or "$H_2O_2$" refers to the compound chemically designated as dihydrogen dioxide, having the CAS Reg. No. 7722-84-1. In specific embodiments, the hydrogen peroxide includes water. In further specific embodiments, the hydrogen peroxide is 50% (w/w) hydrogen peroxide in water. The hydrogen peroxide can be present in the composition, in any suitable and effective amount. In specific embodiments, the hydrogen peroxide (e.g., 50% (w/w) hydrogen peroxide in water) can be present in about 1 wt. % to about 15 wt. % of the composition. In more specific embodiments, the hydrogen peroxide (e.g., 50% (w/w) hydrogen peroxide in water) can be present in about 2 wt. % to about 10 wt. % of the composition. In more specific embodiments, the hydrogen peroxide (e.g., 50% (w/w) hydrogen peroxide in water) can be present in about 3 wt. % to about 9 wt. % of the composition.

Acid

The term "acid" refers to a substance which reacts with a base. Commonly, acids can be identified as tasting sour, reacting with metals such as calcium, and bases like sodium carbonate. Aqueous acids have a pH of less than 7, where an acid of lower pH is typically stronger. Chemicals or substances having the property of an acid are said to be acidic. As used herein, the acid can be an Arrhenius acid, a Lewis acid, or both. The Arrhenius definition states that acids are substances which increase the concentration of hydronium ions ($H_3O^+$) in solution. Lewis acids are electron-pair acceptors. Examples of Lewis acids include all metal cations, and electron-deficient molecules such as boron trifluoride and aluminium trichloride. Hydronium ions are acids according to both definitions. The acid can include One or more inorganic acids, one or more organic acids, or a combination thereof.

The term "inorganic acid" or "mineral acid" refers to an acid derived from one or more inorganic compounds. A mineral acid is not organic and all mineral acids release hydrogen ions when dissolved in water. Examples of inorganic acids include, e.g., sulfuric acid ($H_2SO_4$), hydrochloric acid (HCl), phosphoric acid ($H_3PO_4$), and nitric acid ($HNO_3$).

The term "organic acid" refers to an organic compound with acidic properties. The most common organic acids are the carboxylic acids, whose acidity is associated with their carboxyl group —COOH. Sulfonic acids, containing the group —$SO_2OH$, are relatively stronger acids. The relative stability of the conjugate base of the acid determines its acidity. Other groups can also confer acidity, usually weakly: —OH, —SH, the enol group, and the phenol group.

Organic compounds containing these groups are generally referred to as organic acids. An example of an organic acid is acetic acid.

Anticorrosive Agent

The term "anticorrosive agent" or "corrosion inhibitor" refers to a compound that, when added to a liquid or gas, decreases the corrosion rate of a material, typically a metal or an alloy. Suitable anticorrosive agents include, e.g., benzotriazole.

The term "benzotriazole" or "BTA" refers to the compound 1H-benzotriazole or 1,2,3-benzotriazole, having the CAS Reg. No. 9.5-14-7, and the chemical structure shown below:

benzotriazole

In specific embodiments, the corrosion inhibitor (e.g., benzotriazole) is present in at least about 0.01 wt. % of the composition. In additional specific embodiments, the corrosion inhibitor (e.g., benzotriazole) is present in about 0.01 wt. % to about 1.0 wt. % of the composition. In additional specific embodiments, the corrosion inhibitor e.g., benzotriazole) is present in about 0.05 wt. % to about 0.2 wt. % of the composition.

Surfactant

The term "surfactant" refers to a compound capable of lowering the surface tension of a liquid, the interfacial tension between two liquids, or that between a liquid and a solid. Surfactants may act as detergents, wetting agents, emulsifiers, foaming agents, and/or dispersants. The surfactant can be non-ionic, anionic or cationic. Additionally, the surfactant can include one or more non-ionic surfactants, one or more anionic surfactants, and/or one or more cationic surfactants. Suitable, non-limiting surfactants include, e.g., Plutonic® poloxamers; 2-butoxyethanol and Tergitol® surfactants.

The surfactant can be present in any suitable and effective amount. For example, in specific embodiments, the surfactant can be present in a combined amount of about 0.1 wt. % to about 20 wt. % of the composition. In further specific embodiments, the surfactant can be present in a combined amount of about 0.25 wt. % to about 15 wt % of the composition. In further specific embodiments, the surfactant can be present in a combined amount of about 0.5 wt. % to about 10 wt. % of the composition.

In additional specific embodiments, the surfactant can include Plutonic® L44 polaxamer 124, present in about 0.1 wt. % to about 1.0 wt. % of the composition. In additional specific embodiments, the surfactant can include 2-butoxyethanol, present in about 0.5 wt. % to about 10.0 wt. % of the composition. In additional specific embodiments, the surfactant can include Tergitol® 15-S-12 surfactant, present in about 0.1 wt. % to about 5.0 wt. % of the composition. In additional specific embodiments, the surfactant can include Plutonic® L44 polaxamer 124, present in about 0.1 wt. % to about 1.0 wt. % of the composition; 2-butoxyethanol, present in about 0.5 wt. % to about 10.0 wt. % of the composition; and Tergitol® 15-S-12 surfactant, present in about 0.1 wt. % to about 5.0 wt. % of the composition.

The term "non-ionic surfactant" or "nonionic surfactant" refers to a surfactant, in which the total number of electrons is equal to the total number of protons, giving it a net neutral or zero electrical charge. One suitable class of non-ionic surfactants includes the Pluronics® poloxamers. Another suitable class of non-ionic surfactants includes the Tergitol® surfactants.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade name Pluronics®.

Because the lengths of the polymer blocks can be customized, many different poloxamers exist, that have slightly different properties. For the generic term "poloxamer," these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

The term "Pluronic® L44 surfactant Poloxamer 124 block copolymer" refers to specific nonionic triblock copolymers composed of a central hydrophobic chain of polyoxypropylene (poly(propylene oxide)) flanked by two hydrophilic chains of polyoxyethylene (poly(ethylene oxide)). In specific embodiments, the Pluronic® L44 surfactant Poloxamer 124 block copolymer is present in at least about 2.0 wt. % of the composition. In additional specific embodiments, the Pluronic® L44 surfactant Poloxamer 124 block copolymer is present in about 2.0 wt. % to about 8 wt. % of the composition.

Additional suitable classes of non-ionic surfactants include, e.g., alkyl polyglucosides (e.g., TRITON™ BG-10 Surfactant, TRITON™ CG-50 Surfactant, TRITON™ CG-600 Surfactant, TRITON™ CG-650 Surfactant, TRITON™ CG-110 Surfactant); branched Secondary Alcohol Ethoxylates (e.g., TERGITOL™ TMN Series); Ethylene Oxide/Propylene Oxide Copolymers (e.g., TERGITO™ L Series, TERGITOL™ XD, XH, and XJ Surfactants); Low Foam Surfactants (e.g., ECOSURF™ LF Surfactants, TRITON™ CF Surfactants, TRITON™ DF Surfactants, and TERGITOL™ MinFoam Surfactants); Nonylphenol Ethoxylates (e.g., TERGITOL™ NP Series); Octylphenol Ethoxylates (e.g., TRITON™ X Series), Secondary Alcohol Ethoxylates (e.g., TERGITOL™ 15-S Series); Seed Oil Surfactants (e.g., ECOSURF™ SA Surfactants); Specialty Alkoxylates (e.g., TRITON™ CA Surfactant, TRITON™ N-57 Surfactant, and TRITON™ X-207 Surfactant); and Specialty Ethoxylates (e.g., ECOSURF™ EH Surfactants).

The term "anionic surfactant" refers to a surfactant in which the total number of electrons is greater than the total number of protons, giving it a net negative electrical charge.

The term "cationic surfactant" refers to a surfactant, in which the total number of electrons is less than the total number of protons, giving it a net positive electrical charge.

pH

In specific embodiments, the composition of the present invention can have a pH of less than about 4.5. In further specific embodiments, the composition of the present invention can have a pH of less than about 4.0. In further specific embodiments, the composition of the present invention can have a pH of less than about 3.5. In further specific embodiments, the composition of the present invention can have a pH of less than about 3.0. In further specific embodiments, the composition of the present invention can have a pH of less than about 2.5.

In additional specific embodiments, the composition of the present invention can have a pH of about 2.0 to about 4.5. In further specific embodiments, the composition of the present invention can have a pH of about 2.5 to about 4.0. In further specific embodiments, the composition of the present invention can have a pH of about 2.5 to about 3.5.

Antimicrobial Agent

The compositions described herein can optionally include one or more antimicrobial agents. For example, in specific embodiments, the composition described herein can omit an antimicrobial agent (i.e., antimicrobial agent is absent). In alternative embodiments, the composition described herein include an antimicrobial agent (i.e., antimicrobial agent is present).

As used herein, an "antimicrobial agent" refers to a substance that kills a microorganism, inhibits the growth of a microorganism, or both. Typically, an antimicrobial kills a microorganism or inhibits their growth by cell wall damage, inhibition of cell wall synthesis, alteration of cell wall permeability, inhibition of the synthesis of proteins and nucleic acids, and inhibition of enzyme action. In specific embodiments, the antimicrobial agent is relatively inexpensive, safe, non-toxic, and/or convenient to use.

The antimicrobial agent can be a solid, liquid, or oil.

Any suitable antimicrobial agent can be employed, provided the antimicrobial agent effectively kills a microorganism, inhibits the growth of a microorganism, or both. Suitable specific classes of antimicrobial agents include, e.g., quaternary ammonium compound, a silver-containing compound, a phenol containing compound, a secondary or tertiary nitrogen containing compound, an aldehyde containing compound, a peroxygen containing compound Suitable specific antimicrobial agents include:

TPAC is 3-(trimethoxysilyl)propyl dimethyl octadecyl ammonium chloride. TPAC is also known as Dow Corning 5700 (DC 5700);

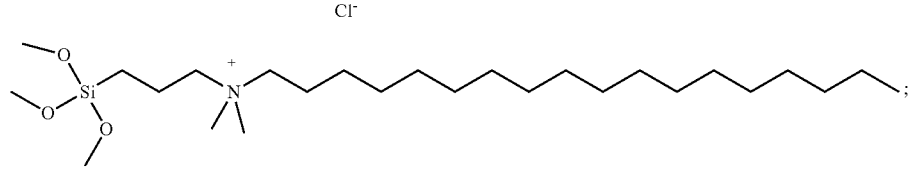

poly(hexamethylene biguanide) hydrochloride (PHMB)

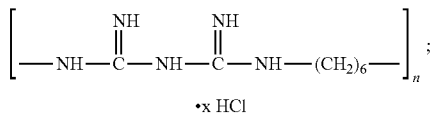

sialic acid (N-acetyl-neuraminic acid, Neu5Ac, NAN, NANA)

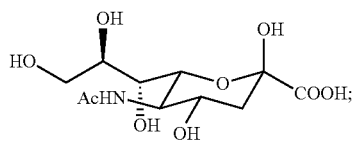 [SMILES: CC(=O)NC1C(O)CC(O)(C(=O)O)OC1[C@H](O)[C@H](O)CO]

poly(diallyldimethylammonium chloride) (poly DADMAC)

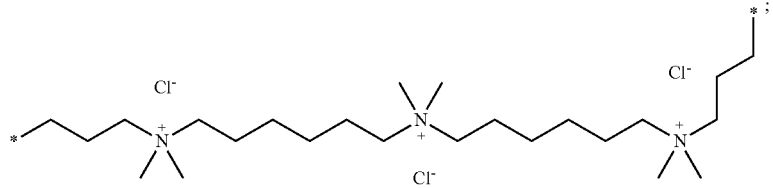

poly (vinyl benzyltrimethyl ammonium chloride) (PVBT-MAC);

5-chloro-2-(2,4-dichlorophenoxy)phenol;

alkyldimethylbenzylammonium chloride (ADBAC);

2,4,4'-trichloro-2'-hydroxydiphenyl ether

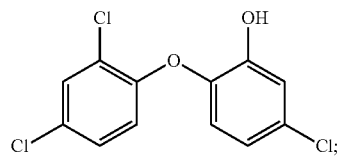

methylisothiazolinone

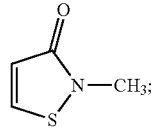

[N-(2-hydroxyl)propyl-3-trimethylammonium chitosan chloride] (HTCC); and a silver complex of poly(amidoamine) (PAMAM); 2,4,4'-trichloro-2'-hydroxydiphenyl ether

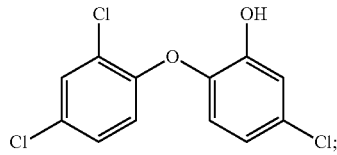 [SMILES: Oc1cc(Cl)ccc1Oc1ccc(Cl)cc1Cl]

methylisothiazolinone

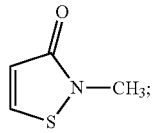

[N-(2-hydroxyl)propyl-3-tritmethylammonium chitosan chloride] (HTCC); and a silver complex of poly(amidoamine) (PAMAM); 2-isopropyl-5-methylphenol; and Poly-D-glucosamine.

The antimicrobial agent can be employed in any suitable amount, provided the amount of antimicrobial agent is effective to kill a microorganism, inhibit the growth of a microorganism, or both. For example, the antimicrobial agent can be employed in up to about 10 wt. % of the liquid composition, in about 0.01 to about 10.0 wt. % of the liquid composition, in about 0.01 to about 5.0 wt. % of the liquid composition, or in about 0.1 to about 2.0 wt. % of the liquid composition. Specifically, the antimicrobial agent can be employed in up to about 80 wt. % of the solid composition, in about 0.1 to about 80.0 wt. % of the solid composition, in about 0.1 to about 50.0 wt. % of the solid composition, or in about 1 to about 50.0 wt. % of the solid composition.

In specific embodiments, the antimicrobial agent can be present and can include 3-(trimethoxysityl)propyl dimethyl octadecyl ammonium chloride (TPAC), present in up to about 5 wt. % of the composition, present in up to about 2.5 wt. % of the composition, or present in up to about 1 wt. % of the composition. In further specific embodiments, the antimicrobial agent can be present and can include 3-(trimethoxysilyl)propyl dimethyl octadecyl ammonium chloride (TPAC), present in about 0.1 wt. % to about 2.0 wt % of the composition. In further specific embodiments, the antimicrobial agent can be present and can include 3-(trimethoxysilyl) propyl dimethyl octadecyl ammonium chloride (TPAC), present in about 0.25 wt. % to about 1.0 wt. % of the composition.

The antimicrobial agent can remain relatively stable and retain the antimicrobial properties over extended periods of time. Such a stability and retention of antimicrobial properties will allow the commercial product to be shipped and stored over periods of time and conditions typically encountered with such products. For example, at least about 75 mol. % of the antimicrobial agent can remain stable and retain the antimicrobial properties at about 20° C. and at about 50% relative humidity, when exposed to the atmosphere, for at least about 3 months. Specifically, at least about 90 mol. % of the antimicrobial agent can remain stable and retain the antimicrobial properties at about 20° C. and at about 50% relative humidity, when exposed to the atmosphere, for at least about 3 months. More specifically, at least about 98 mol. % of the antimicrobial agent can remain stable and retain the antimicrobial properties at about 20° C. and at about 50% relative humidity, when exposed to the atmosphere, for at least about 3 months.

The antimicrobial agent can be selected based at least in part upon the safety and toxicity. Such a suitable safety profile will furnish a commercial product with a broader appeal to those consumers desiring a relatively safe and non-toxic product, when practical and feasible. In such embodiments, the antimicrobial agent can be relatively safe and non-toxic. For example, the antimicrobial agent can have a $LD_{50}$ in rats of greater than about 2 g/kg of body mass. Specifically, the antimicrobial agent can have a $LD_{50}$ in rats of greater than about 5 g/kg of body mass. More specifically, the antimicrobial agent can have a $LD_{50}$ in rats of greater than about 10 g/kg of body mass.

Water

The composition includes a suitable and appropriate amount of water. The composition can be manufactured, shipped, sold and/or stored with relatively little water (i.e., as a concentrate), thereby lowering the costs associated with the same. In such embodiments, the concentrate can subsequently be diluted with the appropriate and suitable amount of water, prior to use. In either situation, the composition can be formulated as a liquid, e.g., formulated as a sprayable or atomized liquid, formulated for application with a textile, or formulated for application with a natural or synthetic sponge. In specific embodiments, the synthetic sponge can be manufactured from at least one of low-density polyether, polyvinyl alcohol (PVA), polyester, polyethylene, and polyurethane. In additional specific embodiments, the textile can include cloth, natural fiber, artificial fiber, animal textile (wool, silk), plant textile (cotton, flax, jute), mineral textile (asbestos, glass fibers), synthetic textile (nylon, polyester, acrylic, acramid, spandex, olefin fiber, ingeo, lurex), or a combination thereof. In additional specific embodiments, the textile can be disposable. In additional specific embodiments, the textile can be reusable.

Coating of Substrate

In specific embodiments, the composition can be applied to a substrate, thereby providing a coating or film on the substrate. The coating or film can provide antimicrobial properties to the substrate (e.g., can effectively kill or inhibit a microorganism, can effectively eliminate or lower malodor associated with the growth of a microorganism, and/or can effectively eliminate or lower staining or discoloration of a substrate). When the composition is applied to a substrate to provide a coating or film on the substrate, the resulting film or coating can remain relatively stable and retain the antimicrobial properties over extended periods of time. For example, the coating or film can remain stable and retain the antimicrobial properties for at least about 3 months. Specifically, the coating or film can remain stable and retain the antimicrobial properties for at least about 1 year. More specifically, the coating or film can remain stable and retain the antimicrobial properties for at least about 2 years. More specifically, the coating or film can remain stable and retain the antimicrobial properties for about 3 months to about 12 months.

In additional specific embodiments, the coating or film can remain stable and retain the antimicrobial properties for at least about 24 hours. In further specific embodiments, the coating or film can remain stable and retain the antimicrobial properties for more than about 1 week. In further specific embodiments, the coating or film can remain stable and retain the antimicrobial properties for more than about 1 month. In further specific embodiments, the coating or film can remain stable and retain the antimicrobial properties for more than about 3 months. In further specific embodiments, the coating or film can remain stable and retain the antimicrobial properties for more than about 6 months.

As such, the compositions described herein can be long-lasting, exhibiting antimicrobial activities for extended periods of time. This includes those embodiments in which the composition is formulated as a film or a coating on a substrate, as well as those in which the substrate is treated one or more times with the composition.

Material Compatability

The composition has a relatively high level of material compatibility. In specific embodiments, the composition has a suitable extended shelf-life stability and compatibility, such that at least about 98 wt. % of each substance is present in the composition after 7 months at 20° C. and 1 atm. In additional specific embodiments, the composition has a suitable extended shelf-life stability and compatibility, such that no more than about 1 wt. % of each substance of the composition degrades, decomposes or reacts within 7 months at 20° C. and 1 atm.

Utility

The invention provides for a composition that can achieve a relatively high-level of disinfection, and is relatively safe for use in disinfecting a wide-spectrum of substrates. In achieving a high-level of disinfection, in specific embodiments, the composition can kill and/or inactivate spores. In additional specific embodiments, the composition can kill and/or inactivate a broad spectrum of microorganisms. When the composition includes a stable residual antimicrobial compound (for example, with the use of a quaternary ammonium silane compound, such as 3-(trimethoxysilyl) propyl dimethyl octadecyl ammonium chloride), the composition can provide a combination of high-level disinfection and long-lasting residual effect, without inhibiting its quick kill times.

The term "disinfectant" refers to a substance that when applied to non-living objects, destroys microorganisms that are living on the objects. Disinfection does not necessarily kill all microorganisms, especially nonresistant bacterial spores, it is less effective than sterilization, which is an extreme physical and/or chemical process that kills all types of life.

The composition of the present invention can be used to effectively reduce the number of microbes located upon a substrate. In specific embodiments, the composition can effectively kill and/or inhibit a microorganism (e.g., virus, fungus, mold, slime mold, algae, yeast, mushroom and/or bacterium), thereby disinfecting the substrate. In further specific embodiments, the composition can effectively inactivate a broad spectrum of microorganisms.

In specific embodiments of the present invention, up to about 2 logs of desired microorganism (e.g., P. aeruginosa, S. aureus, E. hirae, M. terrae, M. intracellulare, M. tuberculosis, M. avium and/or M. avium complex) is inactivated, for example, in about 2 minutes, or less. In further specific embodiments, up to about 3 logs of desired microorganism is inactivated, for example, in about 2 minutes, or less. In further specific embodiments, up to about 4 logs of desired microorganism is inactivated, for example, in about 2 minutes, or less. In further specific embodiments, up to about 5 logs of desired microorganism is inactivated, for example, in about 2 minutes, or less. In further specific embodiments, up to about 6 logs of desired microorganism is inactivated, for example, in about 2 minutes, or less. In further specific embodiments, up to about 7 logs of desired microorganism is inactivated, for example, in about 2 minutes, or less.

In additional specific embodiments of the present invention, at least about 2 logs of desired microorganism (e.g., P. aeruginosa, S. aureus, E. hirae, M. terrae, M. intracellulare, M. tuberculosis, M. avium and/or M. avium complex) is inactivated, for example, in about 2 minutes, or less. In further specific embodiments, at least about 3 logs of desired microorganism is inactivated, for example, in about 2 minutes, or less. In further specific embodiments, at least about 4 logs of desired microorganism is inactivated, for example, in about 2 minutes, or less. In further specific embodiments, at least about 5 logs of desired microorganism is inactivated, for example, in about 2 minutes, or less. In further specific embodiments, at least about 6 logs of desired microorganism is inactivated, for example, in about 2 minutes, or less. In further specific embodiments, at least about 7 logs of desired microorganism is inactivated, for example, in about 2 minutes, or less.

In additional specific embodiments, the composition can effectively sanitize a substrate, thereby simultaneously cleaning and disinfecting the substrate. In additional specific embodiments, the composition can effectively kill or inhibit all forms of life, not just microorganisms, thereby acting as a biocide.

In specific embodiments, the composition can effectively disinfect a substrate. In further specific embodiments, the composition can effectively disinfect the surface of a substrate. In additional specific embodiments, the composition can effectively sterilize a substrate. In further specific embodiments, the composition can effectively sterilize the surface of a substrate.

The composition of the present invention can be formulated for application, depending upon the user's preference as well as the ultimate application of the composition. For example, the composition can be formulated for use in a sprayable composition, atomized liquid sprayer, or liquid applicator. Such formulations can include at least one of a spray bottle, motorized sprayer, wipe, cloth, sponge, non-woven fabric, and woven fabric. Such formulations may be particularly suitable for applying the composition to a surface of a hospital, physician's office, medical clinic, medical facility, dental office, dental facility, airport, school, pet store, zoo, children's day care, elderly nursing home, museum, movie theatre, athletic facility, sporting arena, gymnasium, rest room, bathroom, shopping center, amusement park, church, synagogue, mosque, temple, restaurant, food processing facility, food manufacturing facility, pharmaceutical company, hot-tub, sauna, and/or clean room.

Such liquid formulations may be particularly suitable for applying the composition to metal, plastic, natural rubber, synthetic rubber, glass, stone, grout, fiberglass, wood, concrete, construction products, and/or building products.

In specific embodiments, the composition of the invention can be configured for use in contacting at least one of medical equipment, medical device (e.g., reusable medical device or instrument, such as a colonoscope), surface in the medical industry, dental equipment, dental device, and surface in the dental industry. In a further specific embodiment, the composition of the invention can be configured for use in contacting a medical device (e.g., reusable medical device or instrument).

The term "microbe," "microbes" "microorganism," or "micro-organism" refers to a microscopic organism that comprises either a single cell (unicellular), cell clusters, or no cell at all (acellular). Microorganisms are very diverse; they include bacteria, fungi, archaea, and protists; microscopic plants (green algae); and animals such as plankton and the planarian. Some microbiologists also include viruses, but others consider these as non-living. Most Microorganisms are unicellular (single-celled), but this is not universal, since some multicellular organisms are microscopic, while some unicellular protists and bacteria, like *Thiomargarita namibiensis*, are macroscopic and visible to the naked eye.

The term "virus" refers to a small infectious agent that can replicate only inside the living cells of organisms. Virus particles (known as virions) consist of two or three parts: the genetic material made from either DNA or RNA, long molecules that carry genetic information; a protein coat that protects these genes; and in some cases an envelope of lipids that surrounds the protein coat when they are outside a cell. The shapes of viruses range from simple helical and icosahedral forms to more complex structures. The average virus is about one one-hundredth the size of the average bacterium. An enormous variety of genomic structures can be seen among viral species; as a group they contain more structural genomic diversity than plants, animals, archaea, or bacteria. There are millions of different types of viruses, although only about 5,000 of them have been described in detail. A virus has either DNA or RNA genes and is called a DNA virus or a RNA virus respectively. The vast majority of viruses have RNA genomes. Plant viruses tend to have single-stranded RNA genomes and bacteriophages tend to have double-stranded DNA genomes.

The term "hepatitis B" refers to an infectious inflammatory illness of the liver caused by the hepatitis B virus (HBV).

The term "hepatitis C" refers to an infectious disease affecting primarily the liver, caused by the hepatitis C virus (HCV).

The term "HIV-1" or "human immunodeficiency virus type 1" refers to the most common and pathogenic strain of the HIV virus. HIV can be divided into two major types, HIV type 1 (HIV-1) and HIV type 2 (HIV-2). HIV-1 is related to viruses found in chimpanzees and gorillas living in western Africa, while HIV-2 viruses are related to viruses found in sooty mangabeys. HIV-1 viruses may be further divided into groups. The HIV-1 group M viruses predominate and are responsible for the AIDS pandemic. Group M can be further subdivided into subtypes based on genetic sequence data. Sonic of the subtypes are known to be more virulent or are resistant to different medications. Likewise, HIV-2 viruses are thought to be less virulent and transmissible than HIV-1 M group viruses, although HIV-2 is known to cause AIDS.

The term "herpes simplex" refers to a viral disease caused by both herpes simplex virus type 1 (HSV-1) and type 2 (HSV-2). Infection with the herpes virus is categorized into one of several distinct disorders based on the site of infection. Oral herpes, the visible symptoms of which are colloquially called cold sores or fever blisters, is an infection of the face or mouth. Oral herpes is the most common form of infection. Genital herpes, known simply as herpes, is the second most common form of herpes. Other disorders such as herpetic whitlow, herpes gladiatorum, ocular herpes (keratitis), cerebral herpes infection encephalitis, Mollaret's meningitis, neonatal herpes, and possibly Bell's palsy are all caused by herpes simplex viruses.

There are three types of flu viruses, based upon the antigenic type: A, B, and C. The influenza A and B viruses that routinely spread in people (human influenza viruses) are responsible for seasonal flu epidemics each year. Over the course of a flu season, different types (A & B) and subtypes (influenza A) of influenza circulate and cause illness. Influenza A viruses can be broken down into sub-types depending on the genes that make up the surface proteins. Type A flu or influenza A viruses are capable of infecting people as well as animals, although it is more common for people to suffer the ailments associated with this type of flu. Wild birds commonly act as the hosts for this flu virus. Type A flu virus is constantly changing and is generally responsible for the large flu epidemics. The influenza A2 virus (and other variants of influenza) is spread by people who are already infected. The most common flu hot spots are those surfaces that an infected person has touched and rooms where he has been recently, especially areas where the person has been sneezing.

The term "parvovirus" or "parvo" refers to all the viruses in the Parvoviridae taxonomic family, and also refers to the taxonomic name of the Parvovirus genus within the Parvoviridae family.

The term "norovirus" refers to an RNA virus (taxonomic family Caliciviridae) that causes approximately 90% of epidemic nonbacterial outbreaks of gastroenteritis around the world, and may be responsible for 50% of all foodborne outbreaks of gastroenteritis in the United States. Norovirus affects people of all ages. The viruses are transmitted by fecally contaminated food or water, by person-to-person contact, and via aerosolization of the virus and subsequent contamination of surfaces.

The term "fungi" or "fungus" refers to a large and diverse group of eucaryotic microorganisms whose cells contain a nucleus, vacuoles, and mitochondria, Fungi include algae, molds, yeasts, mushrooms, and slime molds. See, Biology of Microorganisms, T. Brock and M. Madigan, 6th Ed., 1991, Prentice Hill (Englewood Cliffs, N.J.). Exemplary fungi include Ascomycetes (e.g., Neurospora, Saccharomyces, Morchella), Basidiomycetes (e.g., Amanita, Agaricus), Zygomycetes (e.g., Mucor, Rhizopus), Oomycetes (e.g., Allomyces), and Deuteromycetes (e.g., Penicillium, Aspergillus).

The term "mold" refers to a filamentous fungus, generally a circular colony that may be cottony, wooly, etc. or glabrous, but with filaments not organized into large fruiting bodies, such as mushrooms. See, e.g., Stedman's Medical Dictionary, 25th Ed., Williams & Wilkins, 1990 (Baltimore, Md.). One exemplary mold is the Basidiomycetes called wood-rotting fungi. Two types of wood-rotting fungi are the white rot and the brown rot. An ecological activity of many fungi, especially members of the Basidiomycetes is the decomposition of wood, paper, cloth, and other products derived from natural sources. Basidiomycetes that attack these products are able to utilize cellulose or lignin as carbon and energy sources. Lignin is a complex polymer in which the building blocks are phenolic compounds. It is an important constituent of woody plants. The decomposition of lignin in nature occurs almost exclusively through the agency of these wood-rotting fungi. Brown rot attacks and decomposes the cellulose and the lignin is left unchanged. White rot attacks and decomposes both cellulose and lignin. See, Biology of Microorganisms, T. Brock and M. Madigan, 6th Ed., 1991, Prentice Hill (Englewood Cliffs, N.J.).

The term "slime molds" refers to nonphototrophic eucaryotic microorganisms that have some similarity to both fungi and protozoa. The slime molds can be divided into two groups, the cellular slime molds, whose vegetative forms are composed of single amoebalike cells, and the acellular slime molds, whose vegetive forms are naked masses of protoplasms of indefinite size and shape called plasmodia. Slime molds live primarily on decaying plant matter, such as wood, paper, and cloth. See, Biology of Microorganisms, T. Brock and M. Madigan, 6th Ed., 1991, Prentice Hill (Englewood Cliffs, N.J.).

The term "algae" refers to a large and diverse assemblage of eucaryotic organisms that contain chlorophyll and carry out oxygenic photosynthesis. See, Biology of Microorganisms, T. Brock and M. Madigan, 6th Ed., 1991, Prentice Hill (Englewood Cliffs, N.J.). Exemplary algae include Green Algae (e.g., Chlamydomonas), Euglenids (e.g., Euglena), Golden Brown Algae (e.g., Navicula), Brown Algae (e.g., Laminaria), Dinoflagellates (e.g., Gonyaulax), and Red Algae (e.g., polisiphonia).

The term "yeast" refers to unicellular fungi, most of which are classified with the Ascomytes. See, Biology of Microorganisms, T. Brock and M. Madigan, 6th Ed., 1991. Prentice Hill (Englewood Cliffs, N.J.).

The term "mushrooms" refer to filamentous fungi that are typically from large structures called fruiting bodies, the edible part of the mushroom. See, Biology of Microorganisms, T. Brock and M. Madigan, 6th Ed., 1991, Prentice Hill (Englewood Cliffs, N.J.).

The term "bacterium" or "bacteria" refers to a large domain of prokaryotic microorganisms. Typically a few micrometers in length, bacteria have a wide range of shapes, ranging from spheres to rods and spirals. Bacteria are present in most habitats on Earth, growing in soil, acidic hot springs, radioactive waste, water, and deep in the Earth's crust, as well as in organic matter and the live bodies of plants and animals, providing outstanding examples of mutualism in the digestive tracts of humans, termites and cockroaches. There are typically about 40 million bacterial cells in a gram of soil and a million bacterial cells in a milliliter of fresh water; in all, there are approximately five nonillion (5×10$^{30}$) bacteria on Earth, forming a biomass that exceeds that of all plants and animals. Most bacteria have not been characterized, and only about half of the phyla of bacteria have species that can be grown in the laboratory.

The term "*P. aeruginosa*" or "*Pseudomonas aeruginosa*" refers to a common bacterium that can cause disease in animals, including humans. It is found in soil, water, skin flora, and most man-made environments throughout the world. It thrives not only in normal atmospheres, but also in hypoxic atmospheres, and has, thus, colonized many natural and artificial environments. It uses a wide range of organic material for food; in animals, the versatility enables the organism to infect damaged tissues or those with reduced immunity. The symptoms of such infections are generalized inflammation and sepsis. If such colonizations occur in critical body organs, such as the lungs, the urinary tract, and kidneys, the results can be fatal. Because it thrives on most surfaces, this bacterium is also found on and in medical equipment, including catheters, causing cross-infections in hospitals and clinics. It is implicated in hot-tub rash.

The term "*S. aureus*" or "*Staphylococcus aureus*" refers to a facultative anaerobic Gram-positive bacterium. It is frequently found as part of the normal skin flora on the skin and nasal passages. It is estimated that 20% of the human population are long-term carriers of *S. aureus*. *S. aureus* is the most common species of staphylococci to cause Staph infections. The reasons *S. aureus* is a successful pathogen are a combination host and bacterial immuno-evasive strategies. One of these strategies is the production of carotenoid pigment staphyloxanthin which is responsible for the characteristic golden colour of *S. aureus* colonies. This pigment acts as a virulence factor, primarily being a bacterial antioxidant which helps the microbe evade the hosts immune system in the form of reactive oxygen species which the host uses to kill pathogens.

*S. aureus* can cause a range of illnesses from minor skin infections, such as pimples, impetigo, boils (furuncles), cellulitis folliculitis, carbuncles, scalded skin syndrome, and abscesses, to life-threatening diseases such as pneumonia, meningitis, osteomyelitis, endocarditis, toxic shock syndrome (TSS), bacteremia, and sepsis. Its incidence is from skin, soft tissue, respiratory, bone, joint, endovascular to wound infections. It is still one of the five most common causes of nosocomial infections, often causing postsurgical wound infections. Each year, some 500,000 patients in American hospitals contract a staphylococcal infection.

Methicillin-resistant *S. aureus*, abbreviated MRSA and often pronounced "mer-sa" (in North America), is one of a number of greatly-feared strains of *S. aureus* which have become resistant to most antibiotics. MRSA strains are most often found associated with institutions such as hospitals, but are becoming increasingly prevalent in community-acquired infections.

The term "*E. hirae*" or "*Enterococcus hirae*" refers to a species of *Enterococcus*.

The term "*M. terrae*" or "*Mycobacterium terrae*" refers to a slow-growing species of *Mycobacterium*. It is an ungrouped member of the third Runy on (nonchromatogenic mycobacteria). It is known to cause serious skin infections, which are relatively resistant to antibiotic therapy.

The term "*Mycobacterium avium* complex," "*M. avium* complex" or "MAC" refers to a group of genetically related bacteria belonging to the genus *Mycobacterium*. It includes *Mycobacterium avium* and *Mycobacterium intracellulare*.

The term "*M. avium*" or "*Mycobacterium avium*" refers to a species of *Mycobacterium*.

The term "*M. intracellulare*" or "*Mycobacterium intracellulare*" refers to a species of *Mycobacterium*.

The term "*Mycobacterium tuberculosis*" refers to a pathogenic bacterial species in the genus *Mycobacterium* and the causative agent of most cases of tuberculosis. *M. tuberculosis* has an unusual, waxy coating on its cell surface (primarily mycolic acid), which makes the cells impervious to Gram staining, so acid-fast detection techniques are used, instead. The physiology of *M. tuberculosis* is highly aerobic and requires high levels of oxygen. Primarily a pathogen of the mammalian respiratory system, MTB infects the lungs. The most frequently used diagnostic methods for TB are the tuberculin skin test, acid-fast stain, and chest radiographs.

The term "*Mycobacterium bovis*" or "*M. bovis*" refers to a species of *Mycobacterium*.

The term "*Salmonella choleraesuis*" refers to the rod-shaped flagellated, facultative anaerobic, Gram-negative bacterium, which is a member of the genus *Salmonella*.

The term "vancomycin-resistant *Enterococcus* (VRE)" refers to bacterial strains of the genus *Enterococcus* that are resistant to the antibiotic vancomycin.

The term "Staph-reduced vancomycin" refers to bacterial strains of the genus *Staphylococcus* that have a reduced susceptibility to the antibiotic vancomycin.

The term "trichophyton mentagrophytes" refers to a species of *Trichophyton*, which can produce penicillin.

In specific embodiments, the composition described herein (and/or article of manufacture that includes the composition described herein) can effectively inactivate the organisms listed in the table below, when used during its validated shelf-life and according the products directions of use.

| Type | Organism | Contact Time at 20° C. | Results |
| --- | --- | --- | --- |
| Mycobacteria | *Mycobacterium bovis* | ≤3 min. | ≥99.99% reduction |
| Vegetative Organisms | *PSEUDOMONAS AERUGINOSA, SALMONELLA CHOLERAESUIS, Staphylococcus aureus,* MRSA, VRE, Staph-Reduced Vancomycin | ≤2 min. | ≥99.99% reduction |
| Fungi | *Trichophyton mentagrophytes* | ≤2 min. | ≥99.99% reduction |
| Virus | Hepatitis B & C, HIV-1, Herpes Type 1 & 2, Influenza A2 | ≤2 min. | ≥99.9% reduction |
| Virus | Norovirus | ≤5 min. | ≥99.99% reduction |

In addition to the initial inactivation, in specific embodiments, the composition described herein (and/or article of manufacture that includes the composition described herein), when used according to directions of use and during its validated shelf life, will have residual action that lasts up to 48 hours against the following microorganisms.

| Type | Organism | Contact Time at 20° C. | Results |
| --- | --- | --- | --- |
| Gram Positive Bacteria | *Staphylococcus aureus* | 24-48 hours | ≥99.9% reduction |
| Gram Negative Bacteria | *Kiebsiella pneumonia* or *Enterobacter aerogenes* | 24-48 hours | ≥99.9% reduction |
| Other | TBD | 24-48 hours | ≥99.9% reduction |

Kits

The kits of the present invention can include, e.g., the composition and/or the article of manufacture, as described herein (e.g., wipe). Additionally, the kit can include a vessel or canister for containing the composition and/or article of manufacture. For example, the kit can include wipe canisters made of high-density polyethylene. Additionally, the wipe canisters can hold, e.g., 160, 6"×6.75", wipes each, or 65, 10"×12", wipes each. Each canister can be sealed with a foil seal that will remain sealed throughout the shelf-life. The kit can also include a case, which can include two or more canisters. For example, the case can hold 6×2 canisters (12 total). The kit can also include instructions of use, or printed indicia (e.g., product label to conform with EPA guidelines and/or requirements for labeling a hard surface disinfectant), for the distributor, retailer, and/or consumer. The instructions or printed indicia can relate to the safe and effective use and/or storage of the product.

ENUMERATED EMBODIMENTS

Specific enumerated embodiments [1] to [56] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] In one embodiment, the present invention provides for a composition that includes:
($C_1$-$C_8$)alkyl substituted with one or more hydroxyl;
hydrogen peroxide ($H_2O_2$);
thymol (2-isopropyl-5-methylphenol);
optionally an antimicrobial agent;
surfactant;
corrosion inhibitor;
acid, sufficient to maintain the pH below about 4.5; and
water,

[2.] In another embodiment, the present invention provides for a composition of the enumerated embodiment above (e.g., enumerated embodiment [1]), that includes less than about 50 wt. % alcohol.

[3.] In another embodiment, the present invention provides for a composition of any one of the enumerated embodiments above (e.g., any one of enumerated embodiments [1]-[2]), that includes less than about 35 wt. % alcohol.

[4.] In another embodiment, the present invention provides for a composition of any one of the enumerated embodiments above (e.g., any one of enumerated embodiments [1]-[3]), wherein the ($C_1$-$C_8$)alkyl substituted with one or more hydroxyl includes isopropyl alcohol (2-propanol).

[5.] In another embodiment, the present invention provides for a composition of any one of the enumerated embodiments above (e.g., any one of enumerated embodiments [1]-[4]), wherein the ($C_1$-$C_8$)alkyl substituted with one or more hydroxyl includes isopropyl alcohol (2-propanol), in about 10 wt. % to about 30 wt. % of the composition.

[6.] In another embodiment, the present invention provides for a composition of any one of the enumerated embodiments above (e.g., any one of enumerated embodiments [1]-[5]), wherein the hydrogen peroxide ($H_2O_2$) is present in about 2 wt. % to about 6 wt. % of the composition.

[7.] In another embodiment, the present invention provides for a composition of any one of the enumerated embodiments above (e.g., any one of enumerated embodiments [1]-[6]), wherein the thymol (2-isopropyl-5-methylphenol) is present in about 0.05 wt. % to about 1.0 wt. % of the composition.

[8.] In another embodiment, the present invention provides for a composition of any one of the enumerated embodiments above (e.g., any one of enumerated embodiments [1]-[7]), wherein the antimicrobial agent is absent.

[9.] In another embodiment, the present invention provides for a composition of any one of the embodiments above (e.g., any one of enumerated embodiments [1]-[8]), wherein the antimicrobial agent is present.

[10.] In another embodiment, the present invention provides for a composition of any one of the enumerated embodiments above (e.g., any one of enumerated embodiments [1]-[9]), wherein the antimicrobial agent is present, and includes [(3-trimethoxysilyl)propyl] octadecyldimethylammonium chloride (TPAC).

[11.] In another embodiment, the present invention provides for a composition of any one of the enumerated embodiments above (e.g., any one of enumerated embodiments [1]-[10]), wherein the antimicrobial agent is present, and includes ([(3-trimethoxysilyl)propyl] octadecyldimethylammonium chloride) (TPAC), in about 0.25 wt. % to about 1.0 wt. % of the composition.

[12.] In another embodiment, the present invention provides for a composition of any one of the enumerated embodiments above (e.g., any one of enumerated embodiments [1]-[11]), wherein the surfactant includes a non-ionic surfactant.

[13.] in another embodiment, the present invention provides for a composition of any one of the enumerated embodiments [1]-[12]), wherein the surfactant includes at least one of a Pluronic® poloxamer, 2-butoxyethanol and a Tergitol® surfactant.

[14.] In another embodiment, the present invention provides for a composition of any one of the enumerated embodiments above (e.g., any one of enumerated embodiments [1]-[13]), wherein the surfactant is present in a combined amount of about 0.5 wt. % to about 10 wt. % of the composition.

[15.] In another embodiment, the present invention provides for a composition of any one of the enumerated embodiments above (e.g., any one of enumerated embodiments [1]-[14]), wherein the corrosion inhibitor includes benzotriazole.

[16.] In another embodiment, the present invention provides for a composition of any one of the enumerated embodiments above (e.g., any one of enumerated embodiments [1]-[15]), wherein the corrosion inhibitor includes benzotriazole, in about 0.05 wt. % to about 0.2 wt. % of the composition.

[17.] In another embodiment, the present invention provides for a composition of any one of the enumerated embodiments above (e.g., any one of enumerated embodiments [1]-[16]), wherein the composition includes de-ionized water and acid, in an amount sufficient to maintain the pH below about 3.5.

[18.] In another embodiment, the present invention provides for a composition that includes:
  isopropyl alcohol (2-propanol);
  optionally ([(3-trimethoxysilyl)propyl]octadecyldimethylammonium chloride) (TPAC);
  hydrogen peroxide ($H_2O_2$);
  thymol(2-isopropyl-5-methylphenol);
  Pluronic® L44 polaxamer 124;
  2-butoxyethanol;
  Tergitol® 15-S-12 surfactant;
  benzotriazole;
  phosphoric acid; and
  de-ionized water.

[19.] In another embodiment, the present invention provides for a composition that includes:
  about 21 wt. % isopropyl alcohol (2-propanol);
  about 0.5 wt. %) ([(3-trimethoxysilyl)propyl]octadecyldimethylammonium chloride) (TPAC)
  about 4.0 wt % hydrogen peroxide ($H_2O_2$);
  about 0.2 wt. % thymol (2-isopropyl-5-methylphenol);
  about 0.2 wt. % Pluronic® L44 polaxamer 124;
  about 5.0 wt. % 2-butoxyethanol;
  about 0.5 wt. % Tergitol® 15-S-12 surfactant;
  about 0.1 wt % benzotriazole;
  phosphoric acid, sufficient to bring the pH to less than about 3.5; and
  de-ionized water (q.s.).

[20.] In another embodiment, the present invention provides for a composition of any one of the enumerated embodiments above (e.g., any one of enumerated embodiments [1]-[19]), that is formulated as a liquid.

[21.] In another embodiment, the present invention provides for a composition of any one of the enumerated embodiments above (e.g., any one of enumerated embodiments [1]-[20]), that is formulated as a sprayable or atomized liquid.

[22.] In another embodiment, the present invention provides for a composition of any one of the enumerated embodiments above (e.g., any one of enumerated embodiments [1]-[21]), that is formulated for application with a textile.

[23.] In another embodiment, the present invention provides for a composition of any one of the enumerated embodiments above (e.g., any one of enumerated embodiments [1]-[22]), that is formulated for application with a natural or synthetic sponge.

[24.] In another embodiment, the present invention provides for a composition of enumerated embodiment [23], wherein the synthetic sponge is manufactured from at least one of low-density polyether, polyvinyl alcohol (PVA), polyester, polyethylene, and polyurethane.

[25.] In another embodiment, the present invention provides for a composition of any one of the enumerated embodiments above (e.g., any one of enumerated embodiments [1]-[24]), having a suitable extended shelf-life stability and compatibility, such that at least about 98 wt. % of each substance is present in the composition after 7 months at 20° C. and 1 atm.

[26.] In another embodiment, the present invention provides for a composition of any one of the enumerated embodiments above (e.g., any one of enumerated embodiments [1]-[25]), having a suitable extended shelf-life stability and compatibility, such that no more than about 1 wt. % of each substance of the composition degrades, decomposes or reacts within 7 months at 20° C. and 1 atm.

[27.] In another embodiment, the present invention provides for a composition of any one of the enumerated embodiments above e.g., any one of enumerated embodiments [1]-[26]), that is an effective disinfectant.

[28.] In another embodiment, the present invention provides for a composition of any one of the enumerated embodiments above (e.g., any one of enumerated embodiments [1]-[27]), that is an effective surface disinfectant

[29.] In another embodiment, the present invention provides for a composition of any one of the enumerated embodiments above (e.g., any one of enumerated embodiments [1]-[28]), that is an effective sterilant.

[30.] In another embodiment, the present invention provides for a composition of any one of the enumerated embodiments above (e.g., any one of enumerated embodiments [1]-[29]), that is an effective surface sterilant.

[31.] In another embodiment, the present invention provides for a composition of any one of the enumerated embodiments above (e.g., any one of enumerated embodiments [1]-[30]), that can effectively inactivate up to about 6 logs of *Mycobacterium terrae* in about 2 minutes or less.

[32.] In another embodiment, the present invention provides for a composition of any one of the enumerated embodiments above (e.g., any one of enumerated embodiments [1]-[31]), formulated for use on a surface to effectively provide a stable residual coating having antimicrobial activity.

[33.] In another embodiment, the present invention provides for a composition of any one of the enumerated embodiments above (e.g., any one of enumerated embodiments [1]-[32]), formulated for use on a surface to effectively provide a stable residual coating having antimicrobial activity for at least about 24 hours

[34.] In another embodiment, the present invention provides for a composition of any one of the enumerated embodiments above (e.g., any one of enumerated embodiments [1]-[33]), formulated for use on a surface to effectively provide a stable residual coating having antimicrobial activity for more than about 1 week.

[35.] in another embodiment, the present invention provides for a composition of any one of the enumerated embodiments above (e.g., any one of enumerated embodiments [1]-[34]), formulated for use on a surface to effectively provide a stable residual coating having antimicrobial activity for more than about 1 month.

[36.] In another embodiment, the present invention provides for a composition of any one of the enumerated embodiments above (e.g., any one of enumerated embodiments [1]-[35]), formulated for use on a surface to effectively provide a stable residual coating having antimicrobial activity for more than about 3 months.

[37.] In another embodiment, the present invention provides for a composition of any one of the enumerated embodiments above (e.g., any one of enumerated embodiments [1]-[36]), that can effectively inactivate a broad spectrum of microorganisms.

[38.] In another embodiment, the present invention provides for a composition of any one of the enumerated embodiments above (e.g., any one of enumerated embodiments [1]-[37]), that is safe and effective for use with: medical equipment, a surface in the medical industry, dental equipment, a surface in the dental industry, or a combination thereof.

[39.] In another embodiment, the present invention provides for an article of manufacture that includes a textile and a composition,
the composition is located on the surface of the textile, the composition is at least partially embedded within the textile, or a combination thereof, and
wherein the composition is recited in any one of the enumerated embodiments above (e.g., any one of enumerated embodiments [1]-[38]).

[40.] In another embodiment, the present invention provides for an article of manufacture of the enumerated embodiment above (e.g., enumerated embodiment [39]), wherein the textile includes cloth, natural fiber, artificial fiber, animal textile (wool, silk), plant textile (cotton, flax, jute), mineral textile (asbestos, glass fibers), synthetic textile (nylon, polyester, acrylic, acramid, spandex, olefin fiber, ingeo, lurex), or a combination thereof.

[41.] In another embodiment, the present invention provides for an article of manufacture of any one of the enumerated embodiments above (e.g., any one of enumerated embodiments [39]-[40]), wherein the textile is disposable.

[42.] In another embodiment, the present invention provides for an article of manufacture of any one of the enumerated embodiments above (e.g., any one of enumerated embodiments [39]-[41]), wherein the textile is reusable.

[43.] In another embodiment, the present invention provides for an article of manufacture of any one of the enumerated embodiments above (e.g., any one of enumerated embodiments [39]-[42]), that is safe and effective for use with: medical equipment, a surface in the medical industry, dental equipment, a surface in the dental industry, or a combination thereof.

[44.] In another embodiment, the present invention provides for a method of reducing the number of microbes located upon a substrate, the method includes contacting the substrate with an effective amount of the composition or article of manufacture of any one of the enumerated embodiments above (e.g., any one of enumerated embodiments [1]-[38] and [39]-[43], respectively), for a sufficient period of time, effective to reduce the number of microbes located upon the substrate.

[45.] In another embodiment, the present invention provides for a method of killing or inhibiting a microorganism, the method including contacting the microorganism with an antimicrobially effective amount of the composition or article of manufacture of any one of the enumerated embodiments above (e.g., any one of enumerated embodiments [1]-[38] and [39]-[43], respectively), for a sufficient period of time, effective to kill or inhibit the microorganism.

[46.] In another embodiment, the present invention provides for a method of disinfecting a substrate, the method including contacting the substrate with an effective amount of the composition or article of manufacture of any one of the enumerated embodiments above any one of enumerated embodiments [1]-[38] and [39]-[43], respectively), for a sufficient period of time, effective to disinfect the substrate.

[47.] In another embodiment, the present invention provides for a method of any one of the enumerated embodiments above (e.g., any one of enumerated embodiments [44]-[46]), wherein the microbe or microorganism includes at least one of a virus, fungus, mold, slime mold, algae, yeast, mushroom and bacterium.

[48.] In another embodiment, the present invention provides for a method of any one of the enumerated embodiments above (e.g., any one of enumerated embodiments [44]-[47]), wherein up to about 6 logs of desired microorganism is inactivated in about 2 minutes, or less.

[49.] In another embodiment, the present invention provides for a method of any one of the enumerated embodiments above (e.g., any one of enumerated embodiments [44]-[48]), wherein up to about 6 logs of at least one of *P. aeruginosa, S. aureus, E. hirae, M. terrae, M. intracellulare, M. tuberculosis* and *M. avium, M. bovis, Salmonella choleraesuis*, Methicillin-resistant *S. aureus* (MRSA), vancomycin-resistant *Enterococcus* (VRE), staph-reduced vancomycin, trichophyton mentagrophytes, hepatitis B, hepatitis C, HIV-1, herpes type 1, herpes type 2, influenza A2, parvovirus, and norovirus is inactivated in about 2 minutes, or less.

[50.] In another embodiment, the present invention provides for a method of any one of the enumerated embodiments above (e.g., any one of enumerated embodiments [44]-[49]), wherein up to about 6 logs of *Mycobacterium terrae* or *Mycobacterium tuberculosis* is inactivated in about 2 minutes, or less.

[51.] In another embodiment, the present invention provides for a method of any one of the enumerated embodiments above (e.g., any one of enumerated embodiments [44]-[50]), wherein a residual coating having antimicrobial activity is present on the surface of the substrate.

[52.] In another embodiment, the present invention provides for a method of enumerated embodiment [51], wherein the residual coating having antimicrobial activity is present on the surface of the substrate for at least about 24 hours.

[53.] In another embodiment, the present invention provides for a method of enumerated embodiment [51], wherein the residual coating having antimicrobial activity is present on the surface of the substrate for at least about 1 week.

[54.] In another embodiment, the present invention provides for a method of enumerated embodiment [51], Wherein the residual coating having antimicrobial activity is present on the surface of the substrate for at least about 1 month.

[55.] In another embodiment, the present invention provides for a method of enumerated embodiment [51], wherein the residual coating having antimicrobial activity is present on the surface of the substrate for at least about 3 months.

[56.] In another embodiment, the present invention provides for a method of enumerated embodiment [51], wherein the residual coating having antimicrobial activity is present on the surface of the substrate for at least about 6 months.

EXAMPLE

The present invention provides for the following GLP tests performed with a wetted wipe.

|  | (min.) | Log Reduction |
|---|---|---|
| Virus | | |
| Influenza A2 | 2 | ≥4 |
| HIV-1 | 2 | ≥4 |
| HBV | 2 | ≥4 |
| HCV | 2 | ≥4 |
| Herpes 1 | 2 | ≥4 |
| Herpes 2 | 2 | ≥4 |
| Parvovirus | 5 | ≥4 |
| Norovirus | 5 | ≥4 |
| Bacteria | | |
| *Mycobacterium bovis* (TB) | 2 | ≥4 |
| *Salmonella enterica* | 2 | ≥5 |
| MRSA | 2 | ≥4 |
| VRE | 2 | ≥4 |
| *Staphylococcus aureus* | 2 | ≥5 |
| *Pseudomonas aeruginosa* | 2 | ≥5 |
| Staph reduced Vancomycin | 2 | ≥4 |
| Fungus | | |
| *Trichophyton mentagrophytes* | 2 | ≥4 |

What is claimed is:

1. A composition comprising:
   ($C_1$-$C_8$)alkyl substituted with one or more hydroxyl;
   hydrogen peroxide ($H_2O_2$);
   thymol (2-isopropyl-5-methylphenol);
   an antimicrobial agent comprising ([(3-trimethoxysilyl)propyl]octadecyldimethylammonium chloride) (TPAC);
   surfactant;
   corrosion inhibitor;
   acid, sufficient to maintain the pH below about 4.5; and
   water.

2. The composition of claim 1, comprising less than about 50 wt. % alcohol.

3. The composition of claim 1, comprising less than about 35 wt. % alcohol.

4. The composition of claim 1, wherein the ($C_1$-$C_8$)alkyl substituted with one or more hydroxyl comprises isopropyl alcohol (2-propanol).

5. The composition of claim 1, wherein the ($C_1$-$C_8$)alkyl substituted with one or more hydroxyl comprises isopropyl alcohol (2-propanol), in about 10 wt. % to about 30 wt. % of the composition.

6. The composition of claim 1, wherein the hydrogen peroxide ($H_2O_2$) is present in about 2 wt. % to about 6 wt. % of the composition.

7. The composition of claim 1, wherein the thymol (2-isopropyl-5-methylphenol) is present in about 0.05 wt. % to about 1.0 wt. % of the composition.

8. The composition of claim 1, wherein the antimicrobial agent is present in a range of about 0.25 wt. % to about 1.0 wt. % of the composition.

9. The composition of claim 1, wherein the surfactant comprises a non-ionic surfactant.

10. The composition of claim 1, wherein the surfactant comprises at least one of a nonionic triblock copolymer surfactant composed of a central hydrophobic chain of polyoxypropylene (poly(propylene oxide)) flanked by two hydrophilic chains of polyoxyethylene (poly(ethylene oxide)), 2-butoxyethanol and a nonionic alkyl polyglucoside surfactant.

11. The composition of claim 1, wherein the surfactant is present in a combined amount of about 0.5 wt. % to about 10 wt. % of the composition.

12. The composition of claim 1, wherein the corrosion inhibitor comprises benzotriazole.

13. The composition of claim 1, wherein the corrosion inhibitor comprises benzotriazole, in about 0.05 wt. % to about 0.2 wt. % of the composition.

14. The composition of claim 1, wherein the composition comprises de-ionized water and acid, in an amount sufficient to maintain the pH below about 3.5.

\* \* \* \* \*